(12) United States Patent
Thomke et al.

(10) Patent No.: US 9,943,385 B2
(45) Date of Patent: Apr. 17, 2018

(54) MANUFACTURING AN INNER STRUCTURE FOR A CERAMIC IMPLANT AND FOR A CERAMIC ATTACHMENT ELEMENT

(71) Applicant: Z-Systems Schweiz AG, Oensingen (CH)

(72) Inventors: Ernst Thomke, Grenchen (CH); Roger Staudenmann, Busswil b. Buren (CH); Thomas Hug, Erlenbach (CH); Rubino Di Girolamo, Oberageri (CH)

(73) Assignee: Z-SYSTEMS SCHWEIK AG, Oensingen (CH)

( * ) Notice: Subject to any disclaimer, the term of this patent is extended or adjusted under 35 U.S.C. 154(b) by 0 days.

(21) Appl. No.: 14/035,330

(22) Filed: Dec. 9, 2013

(65) Prior Publication Data
US 2014/0162210 A1    Jun. 12, 2014

(30) Foreign Application Priority Data

Sep. 26, 2012    (CH) ...................................... 1744/12

(51) Int. Cl.
*A61C 8/00* (2006.01)
(52) U.S. Cl.
CPC .............. *A61C 8/00* (2013.01); *A61C 8/0012* (2013.01); *Y10T 29/49567* (2015.01)
(58) Field of Classification Search
CPC .. Y10T 29/49567; A61C 8/0012; B24B 19/02
See application file for complete search history.

(56) References Cited

U.S. PATENT DOCUMENTS

| | | | | |
|---|---|---|---|---|
| 3,121,297 A * | 2/1964 | Brady | ....................... | B23F 1/02 451/211 |
| 4,083,152 A * | 4/1978 | Lorenz | ................ | B23F 23/1262 451/363 |
| 4,735,019 A * | 4/1988 | Wiederkehr | ............ | B24B 19/02 451/215 |
| 4,766,704 A * | 8/1988 | Brandestini | ........ | A61C 13/0003 451/58 |
| 5,782,918 A * | 7/1998 | Klardie | ................... | A61C 8/005 433/172 |
| 6,332,777 B1 * | 12/2001 | Sutter | ................... | A61C 8/0001 433/173 |
| 7,162,321 B2 * | 1/2007 | Luthardt | ............ | A61C 13/0004 264/16 |
| 7,726,969 B2 * | 6/2010 | Walther | ............... | A61C 8/0012 433/174 |
| 2004/0265781 A1 * | 12/2004 | Coatoam | ................ | A61C 8/005 433/173 |

FOREIGN PATENT DOCUMENTS

| | | |
|---|---|---|
| DE | 10 2005 008 273 | 8/2006 |
| EP | 1 967 157 | 9/2008 |
| WO | 2008/022635 | 2/2008 |
| WO | 2012/128623 | 9/2012 |

* cited by examiner

*Primary Examiner* — Ralph Lewis
(74) *Attorney, Agent, or Firm* — Rankin, Hill & Clark LLP

(57) ABSTRACT

A method for manufacturing an inner structure as an insertion geometry and/or as a rotation lock of a ceramic implant or of a ceramic attachment element. Thereby, a rotating disc for removing ceramic material is advanced in an advance direction of the rotating disc perpendicular to the rotation axis of the disc, into a proximally accessible surface of the ceramic implant or into an end surface of a ceramic attachment element.

8 Claims, 8 Drawing Sheets

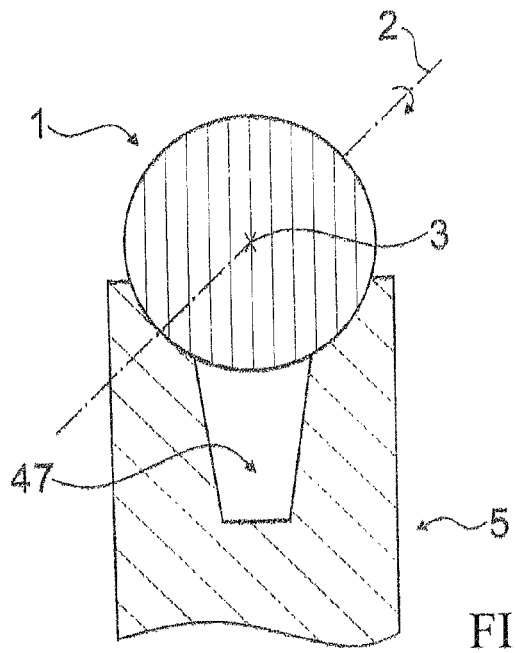
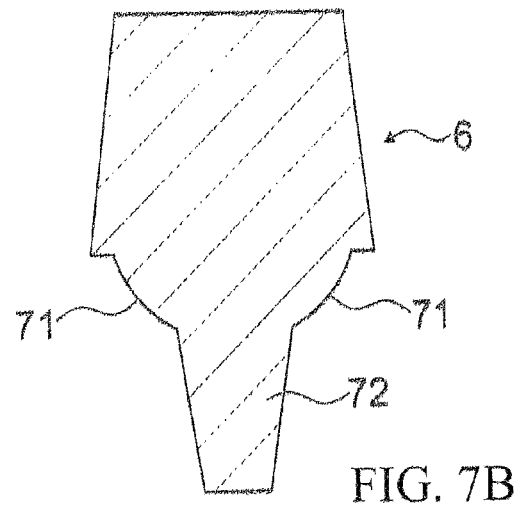
FIG. 7A
FIG. 7B
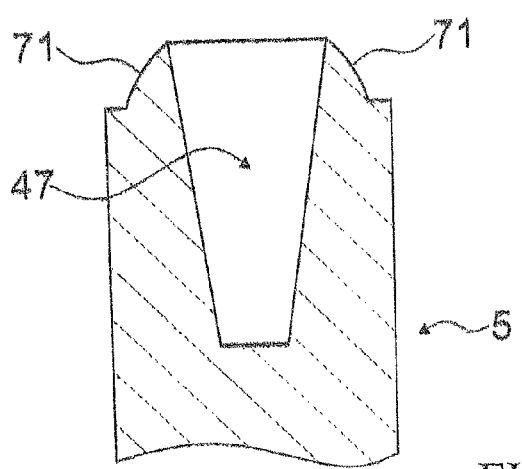
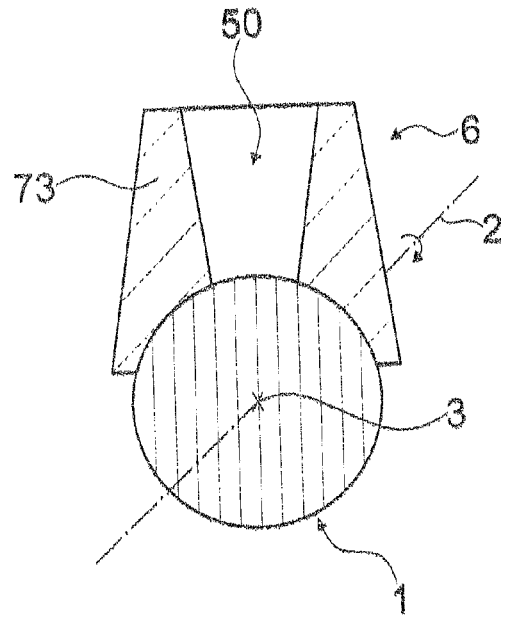
FIG. 8A
FIG. 8B

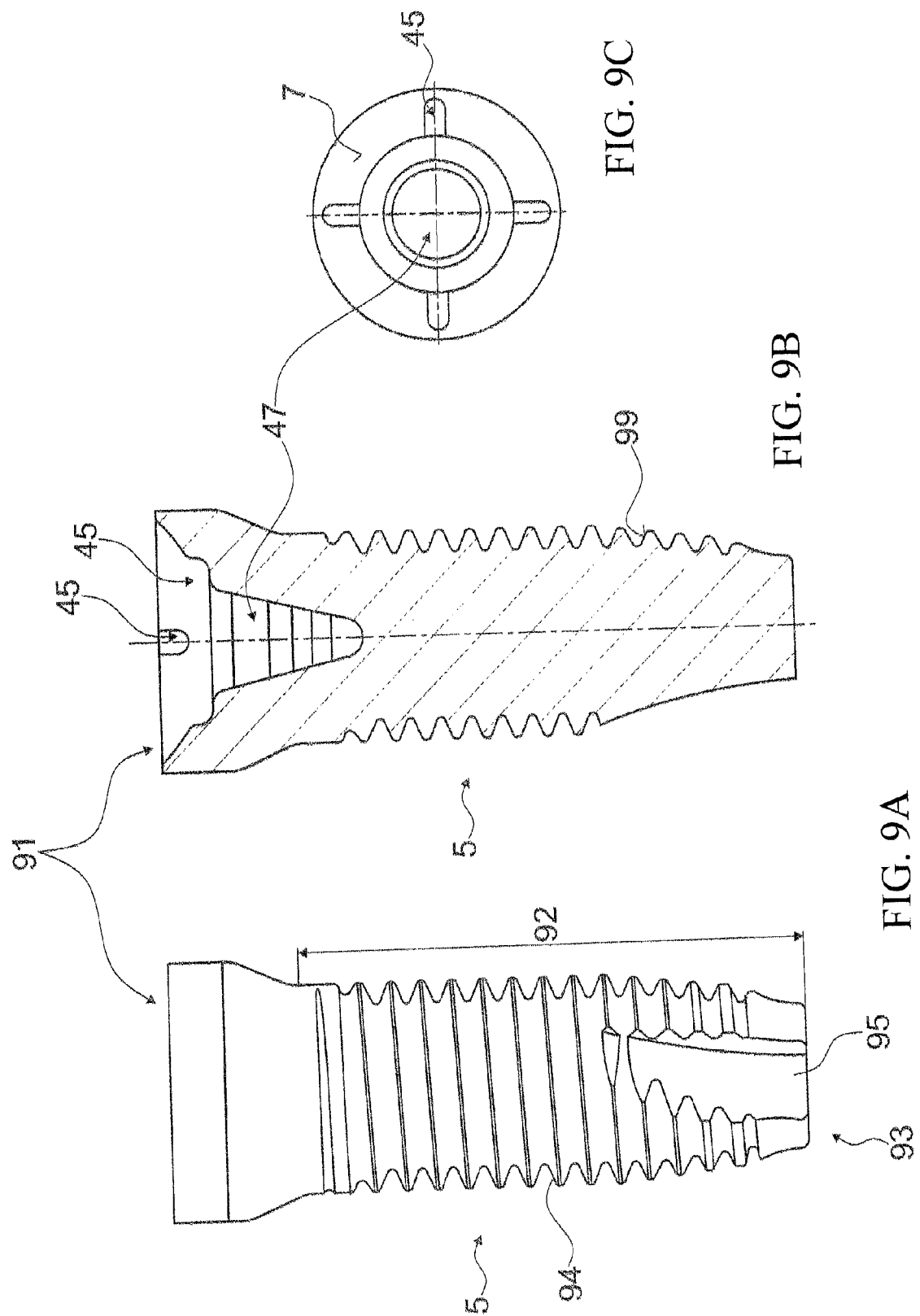

MANUFACTURING AN INNER STRUCTURE FOR A CERAMIC IMPLANT AND FOR A CERAMIC ATTACHMENT ELEMENT

BACKGROUND OF THE INVENTION

Field of the Invention

The present invention generally relates to dental medicine and provides a method for machining a ceramic implant or a ceramic attachment element, for creating an inner structure.

Description of Related Art

Implants manufactured of ceramic are known from the state of the art and, in particular, due to their extraordinary biocompatibility and aesthetic advantages, are often preferable for dental-medical applications compared to conventional implants of titanium and titanium alloys.

Ceramic implants, as is known, are manufactured of oxide ceramics, for example of ceramic based on zirconium oxide or aluminium oxide. The manufacture of implants of titanium or titanium alloys and of ceramic implants is different. The ceramic material is particularly hard and cannot be machined with the same techniques as are common with metal machining. In particular, ceramic material cannot be punched or turned due to its brittle characteristics. The usually applied material-removing methods, in particular grinding for creating outer contours or inner contours of ceramic implants are comparatively time-consuming and thus expensive.

EP 2 072 020 describes such a method for manufacturing dental-medical products of ceramic such as implants, bridges, attachment elements (abutment). In this method, firstly a ceramic green compact containing a binder is manufactured firstly by way of pressing a ceramic powder for example at 180 to 300 MPa. This green compact is machined for example by way of cutting or grinding. The binder is not removed until after this machining when sintering. Further steps of grinding at increasing speeds and with an initially larger diameter of the milling tool are described for increasing the machining efficiency.

Grinding methods with rotating pins are common for creating fine contours and in particular inner contours. This machining step is time-consuming, since ceramic material is often removed only at the end face of the pin, or perpendicularly thereto, wherein in both cases, very little ceramic material is removed per unit of time. Such grinding steps therefore slow down the production of ceramic implants. For this reason, the manufacture of such inner contours with ceramic implants also entails a significantly increased cost factor in comparison to the manufacture of inner contours with conventional implants of titanium or titanium alloys.

SUMMARY OF THE INVENTION

The present invention is directed toward providing a method for machining a ceramic implant or a ceramic attachment element, with which inner contours, in particular for an insertion geometry, a rotational lock or a positioning structure, of a ceramic implant or of a ceramic attachment element can be manufactured in a particularly efficient method. The present invention is also directed toward ceramic implants and ceramic attachment elements for an implant system with inner contours, which can be manufactured particularly efficiently.

In accordance with one aspect of the invention, a method for manufacturing an inner structure as an insertion geometry and/or as a rotation lock, of a ceramic implant or of a ceramic attachment element is provided. Thereby, a rotating disc for removing ceramic material is advanced in an advance direction of the rotating disc perpendicularly to the rotation axis of the disc, into a proximally accessible surface of the ceramic implant or into an end surface of the ceramic attachment element.

The present text defines a "ceramic implant" as a ceramic dental implant that is implantable with at least a distal region into a bone tissue. In some embodiments, the ceramic implant is a pin-like dental implant.

The ceramic implant can be the dental implant of a two-part or multi-part implant system that is anchored in the bone, or it can be a single-part dental implant that is anchored in the bone.

Abutments, for example, transgingival parts such as a transgingival male for a female system are indicated as attachment elements. Such attachment elements comprise a structure for fastening a tertiary part such as crowns, dentures, bridges, caps etc. Crowns, dentures, bridges, caps etc., which are also to be directly fastened on the implant, are also indicated as attachment element. The attachment element is thus not anchored into the bone itself but is fastened directly or indirectly on the implant via one or more further attachment element.

In this text, an "implant system" indicates a dental implant system which, apart from the implant anchored in the bone, comprises at least one attachment element. At least the implant and/or at least an attachment element of the implant system are manufactured of ceramic material. The dental implant system can also contain parts that do not or only partly consist of ceramic, for example an implant of titanium.

The at least one inner structure of the ceramic implant or of the attachment element is a recess of the ceramic implant or ceramic attachment element which is manufacturable with a rotating disc. The rotating disc removes ceramic material of the ceramic implant or of the ceramic attachment element, so that an inner structure of the ceramic implant or of the ceramic attachment element arises due to the recessing of ceramic material and this inner structure serves as an insertion geometry for the ceramic implant and/or as insertion geometry, as a rotational lock and/or as a positioning structure for the connection of the implant to the ceramic attachment element or between two attachment elements.

The inner structure of the insertion geometry is compatible with an outer structure of an insertion tool and/or with an outer structure of an attachment element. The inner structure of the rotation lock or of the positioning structure is compatible with an outer structure of an implant or of a further attachment element. The insert directions of the insertion tool into the insertion geometry or of the outer structure of the attachment element into the rotation lock or into the positioning structure correspond to the advance direction of the rotating disc into the proximally accessible surface of the ceramic implant or into one of the end surfaces of the attachment element.

The insertion geometry serves for screwing the implant into the bone or also for a connection of the attachment element to the implant or of two attachment elements amongst one another, by way of an insertion tool or in some embodiments by way of outer structures of the attachment element. The rotation lock prevents the loosening of a screw connection, in particular between an implant and an attachment element or between two attachment elements. The positioning structure ensures certain relative positions or a selection of relative positions between the implant and the attachment element or between two attachment elements that are connected, for example, with a bonding connection.

The terms "proximal" and "distal" in the present text are used with regard to the implantation direction. Generally, the distal direction corresponds to the direction towards the apical end of the dental implant (or of the tooth root or the tooth), while the proximal direction corresponds to the coronal direction.

The ceramic implant or the ceramic attachment element consists of ceramic material, in particular of an oxide ceramic, such as, for example, ceramic based on zirconium oxide, yttrium-stabilised ceramic based on zirconium oxide or ceramic based on aluminium oxide. In some embodiments, the ceramic implant or the ceramic attachment element are connected to non-ceramic parts of an implant system.

Unless otherwise stated, the term "ceramic implant" or "ceramic attachment element" in this text relates to sintered ceramic bodies as well as also to not yet sintered, intermediate products in the manufacturing method of the ceramic implant or of the ceramic attachment element, so-called green compacts. Moreover, the terms "ceramic implant" and "ceramic attachment element", unless otherwise stated, not only describe the finished manufactured end products but also blanks that have not yet been completely machined or processed and whose outer contours and/or inner contours are not yet completely manufactured. If, in this context, it is clear that it is the case of ceramic parts, the terms ceramic implant or ceramic attachment element are sometimes abbreviated to implant or attachment element.

A proximally accessible surface of the ceramic implant means that the surface, into which the rotating disc is advanced to the inner structure during the manufacture, at least directly after the implantation of the ceramic implant in the bone, remains accessible from the proximal side, and thus is not surrounded by bone tissue. In some embodiments, in particular of the two-part or multi-part implant system, essentially the complete ceramic implant except the proximally accessible surface is surrounded by bone tissue after the implantation. The proximally accessible surface of the implant in some embodiments is an end-face of a ceramic implant, in particular of a pin-like ceramic implant, wherein the end-face is essentially perpendicular to the implant axis.

The end surface of the ceramic attachment element is an inner or outer surface of the attachment element, which in the manufacturing method is accessible for the machining and into which the rotating disc is advanced in a direction perpendicular to its rotation axis.

The proximally accessible surface of the implant or the end surface of the attachment element in some embodiments is flat and in other embodiments is arcuate. In some embodiments, the proximally accessible surface or end surface for example is arranged parallel to the axis, such as for example the lateral surface of an inner or outer cylinder, or it is angled to the axis, for example the lateral surface of an inner or outer cone. The proximally accessible surface or the end surface can extend over several planes for example in a step-like manner. The proximally accessible surface or the end surface can be different or it can be uniform, in different regions.

In some embodiments of the attachment element, an inner structure is manufactured in more that one end surface, for example in two lateral end surfaces or in a distal and a proximal end surface or also in more than two end surfaces.

In accordance with the method, a rotating disc (wheel) is used for removing away ceramic material and is advanced in an advance direction of the rotating disc perpendicularly to the rotation axis of the disc, into a proximally accessible surface of the ceramic implant, or into an end surface of the ceramic attachment element. This means that advantageously, the rotating disc removes away material at both of its disc surfaces. Ceramic material is removed significantly more efficiently and more quickly by way of such a double-sided grinding perpendicular to the rotation axis, than for example by way of a comparably large end-face of a pin that rotates about its longitudinal axis and is advanced parallel to its rotation axis. Thus the insertion geometry, rotation lock and/or positioning structure can be manufactured significantly more quickly and inexpensively with the method according to the invention than with conventional methods. The rotating disc in the following text is abbreviated to grinding disc or disc.

In further accordance with the method, the disc is advanced perpendicularly to the rotation direction of the disc, but not perpendicularly to the proximally accessible surface of the ceramic implant or to the end surface of the ceramic attachment element.

An inner structure with a slot-like opening arises due to the advance of the rotating disc perpendicularly to the rotation axis, into a proximally accessible surface of the implant or into an end surface of the ceramic attachment element. The rotating disc in some embodiments is a shaped grinding disc and thus the grinding tool determines the shape of the inner structure of the implant. In some embodiments, the disc is advanced somewhat less deeply into the proximally accessible surface of the ceramic implant or into the end surface of the ceramic attachment element, than up to the disc centre, through which the rotating rotation axis leads.

In such embodiments of the method, the disc centre during the complete manufacturing method of the inner structure is positioned proximally to the proximally accessible surface of the ceramic implant or proximally to the end surface of the attachment element. A longitudinal section through the slot parallel to the advance direction of the rotating disc advanced into a closed proximally accessible surface or into a closed end surface is then a circle segment (segment of a circle) which is smaller than a semicircle. This circle segment is formed by a chord at the opening of the slot and a circular arc (arc of a circle) in the ceramic implant or ceramic attachment element. The length and depth of the slots is essentially dependent on how deep the disc is advanced into the ceramic implant or into the ceramic attachment element. Both are maximally somewhat shorter than the diameter of the rotating disc. The width of the slot essentially measures the same amount as the width of the disc.

If the rotating disc is advanced more than once at different positions on the proximally accessible surface of the implant or the end surface of the attachment element, then a multi-slot inner structure arises, for example an inner structure with two or more parallel slots or with two or more intersecting or crossing slots. Thereby, equally dimensioned or differently dimensioned rotating discs can be used for manufacturing the multi-slot inner structure.

The slots cross in some embodiments of the ceramic implant or of the ceramic attachment element. In such embodiments, four part-slots arise for example from two intersecting full slots, or six part-slots arise from three intersecting slots, etc. In some of these embodiments, the slots cross or intersect in the respective middle of the slot opening. An inner structure with several part-slots arises by way of this, and the length of these is in each case somewhat less than half that of a full slot.

In some embodiments with crossing slots, parts slots arise, of which an end point of the circular arc lies in the proximally accessible surface of the ceramic implant, while the other end point of the circular arc lies in the inside of the ceramic implant or of the ceramic attachment element, for example at an intersection point with a crossing slot or at an inner wall of a cavity of the ceramic implant or of the ceramic attachment element.

In some embodiments, the proximally accessible surface of the implant or the end surface of the attachment element is not a closed surface but rather borders around or surrounds a cavity in the ceramic implant or in the ceramic attachment element, for example a drilled hole. Such a cavity thus opens into the proximally accessible surface of an implant or into an end surface of an attachment element. In some embodiments of the ceramic implant or of the ceramic attachment element with a cavity, this cavity is rotationally symmetrical, in particular cylindrical or conical. In some of these embodiments with a cavity, the proximally accessible surface of the implant or the end surface of the attachment element is annular. In some embodiments of the ceramic implant or of the attachment element with a cavity, the proximally accessible surface of the implant or the end surface of the attachment element is flush with the opening of the cavity, and in other embodiments the proximally accessible surface of the implant or the end surface of the attachment element is sunk in the cavity. In some embodiments, the proximally accessible surface or the end surface completely borders around the opening of the cavity, and in other embodiments, the proximally accessible surface or the end surface at least partly borders around the opening, for example as an open annular surface.

Thus, in some embodiments of the ceramic implant or of the ceramic attachment element with a cavity, the inner structure not only opens into the proximally accessible surface of the implant or into one or more end surfaces of the attachment element, into which surfaces the disc rotating perpendicularly to the advance direction has been introduced, but additionally also into the cavity. In some embodiments of the ceramic implant or ceramic attachment element, parts-slots arise, whose opening is delimited laterally outwards, thus at the side facing the lateral surface, by the proximally accessible surface of the ceramic implant or of the end surface of the attachment element, said surfaces bordering around the cavity. The part-slots run out into the cavity, at the side facing the cavity.

In some embodiments of the ceramic implant or of the ceramic attachment element with a cavity, this is a central cavity such as a drilled hole with a diameter, for example. A rotating disc with a diameter is selected for the method in some of these embodiments, wherein the disc diameter is larger than the cavity diameter. In such embodiments, inner structures with two part-slots which serve as an insertion geometry, rotation lock structure and/or positioning structure arise due to the advance of the rotating disc perpendicular to the rotation axis of the disc, into the proximally accessible surface of the implant or into an end surface of the attachment element. Inner structures with an even number of part-slots arise by way of repeated advancing of the disc into such embodiments of the ceramic implant or of the ceramic attachment element which are described here.

In further accordance with other embodiments of the method, the rotating disc is selected with a diameter, wherein the disc diameter is smaller than the cavity diameter. In such embodiments, inner structures with a part-slot arise by way of the advance of the rotating disc perpendicular to the rotation axis of the disc, into the proximally accessible surface of the implant or into an end surface of the attachment element. Even such an individual part-slot can serve as an insertion geometry, rotation lock structure and/or positioning structure. An inner structure which has an odd or an even number of part-slots arises by way of repeated advance of the disc with a disc diameter that is smaller than the cavity diameter.

In some embodiments of the method for manufacturing an inner structure of the ceramic implant or of the ceramic attachment element with a cavity, firstly the cavity and after this the inner structure as an insertion geometry, rotation lock or positioning structure is created, whereas the sequence is in the reverse in other embodiments.

Another aspect of the invention relates to a ceramic implant or to a ceramic attachment element with an inner structure that can be manufactured with the method according to the invention.

Inner structures whose longitudinal sections in the plane parallel to the advance direction of the rotating disc have geometric shapes as are defined in the claims and described in the figures, arise by way of the manufacturing method of the inner structures with a rotating disc that is advanced perpendicularly to the rotation axis, into the implant or into the attachment element.

A further aspect of the invention relates to an implant system that comprises a ceramic implant or a ceramic attachment element, with an inner structure that is manufacturable with the method according to the invention and/or that has the characteristics described above. The implant system comprises at least one implant anchored in the bone and at least one attachment element, wherein at least the implant or at least an attachment element is manufactured of ceramic material and has an inner structure that serves as an insertion geometry, rotation lock and/or positioning structure. Thus, the implant of the implant system in some embodiments is a ceramic implant or in other embodiments the implant consists of another material such as titanium or a titanium alloy, for example. In embodiments with a non-ceramic implant, at least one attachment element is a ceramic attachment element with an inner structure as a rotation lock, insertion geometry and/or positioning structure. In embodiments with a ceramic implant and with at least one ceramic attachment element, the at least the ceramic implant or at least a ceramic attachment element comprises an inner structure as a rotation lock, positioning structure and/or insert geometry, wherein this inner structure is manufacturable with the method according to the invention.

Another aspect of the invention relates to a set comprising and an insertion tool and comprising a ceramic element or at least one ceramic attachment element or an implant system with at least one inner structure as an insertion geometry, as has been described above.

BRIEF DESCRIPTION OF THE DRAWINGS

FIG. 7A is a sectional view of a ceramic implant with an inner structure.

FIG. 7B is a sectional view of an attachment element with an outer structure.

FIG. 8A is a sectional view of a ceramic implant with an outer structure.

FIG. 8B is a sectional view of a ceramic attachment element with an inner structure.

FIG. 9A is an elevational view of an example of a bonded, two-part implant system.

FIG. 9B is a section through the implant of FIG. 9A.

FIG. 9C is a view of the proximally accessible surface of the implant FIG. 9A.

DETAILED DESCRIPTION OF THE PREFERRED EMBODIMENTS

Figure 1A:
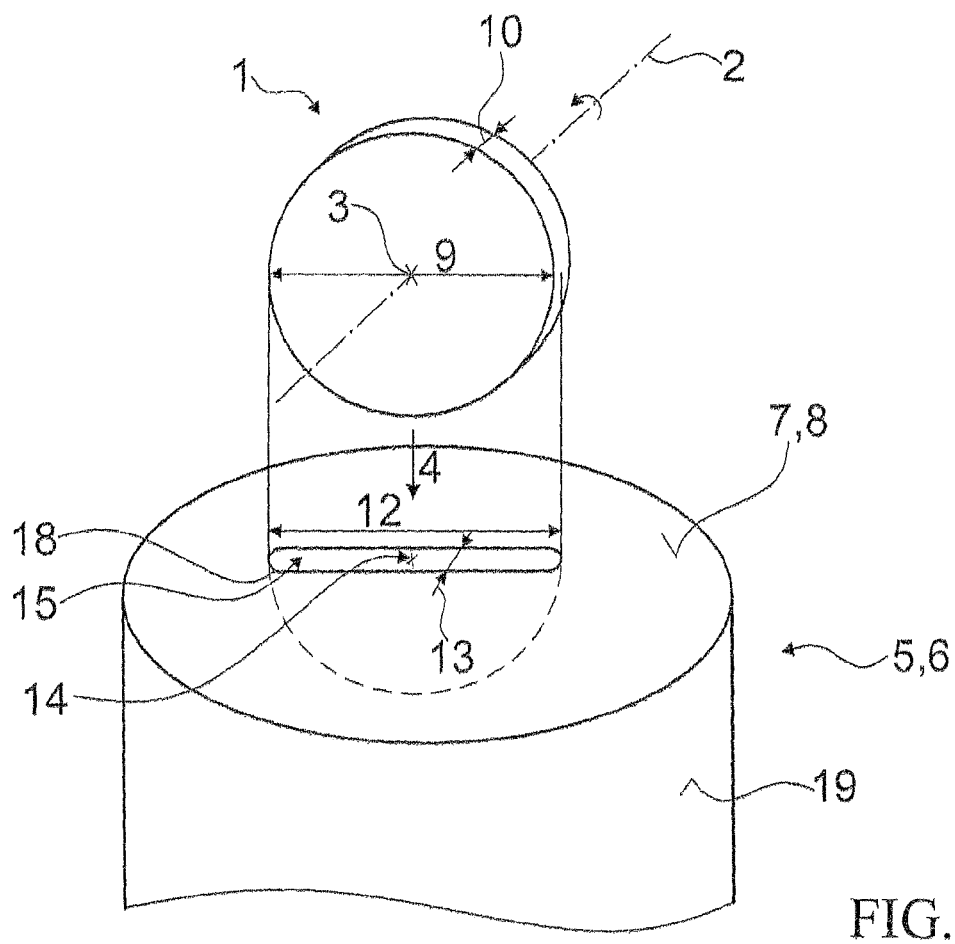
FIGS. 1A and 1B schematically illustrate the method of the present invention.

FIG. 1A a schematic drawing shows an exemplary embodiment of the method for manufacturing an inner structure in a proximally accessible surface 7 of a ceramic implant 5 or in an end surface 8 of a ceramic attachment element 6. The ceramic implant 6 or the ceramic attachment element 5 is fixed in a grinding machine. A disc 1 rotating about a rotation axis 2 is advanced in an advance direction 4 perpendicularly to its rotation axis 2, into the proximally accessible surface 7 of a ceramic implant 5 or into the end surface 8 of the ceramic attachment element 6. By way of this, ceramic material is removed, and an inner structure of the implant or of the attachment element is created.

The rotating disc for example is a metal-bonded or plastic-bonded diamond tool. Metal-bonded diamond tools have a longer service life than plastic-bonded diamond tools, they are however more expensive that the latter. The diamond grain size is for example in the region of 20 to 120 µm, in particular in the region of 46 to 60 µm.

The rotating disc 1 is a shaped grinding disc, and the grinding tool thus determines the shape of the inner structure of the implant 5 or of the attachment element 6. A disc diameter 9 for example measures 2 to 20 mm or also more, and in particular it measures 4 to 10, or 4 to 8 mm, or 5 to 7 mm. A disc diameter in the region of 5 to 7 mm is particularly suitable for creating inner structures in the proximally accessible surface of the implant. A disc width 10 for example measures 0.2 to 4 mm or 0.2 to 3 mm or in particular 0.3 to 2 mm, 0.2 to 1 mm or 0.4 to 0.8 mm or in particular 0.5 to 0.7 mm.

Figure 1B:
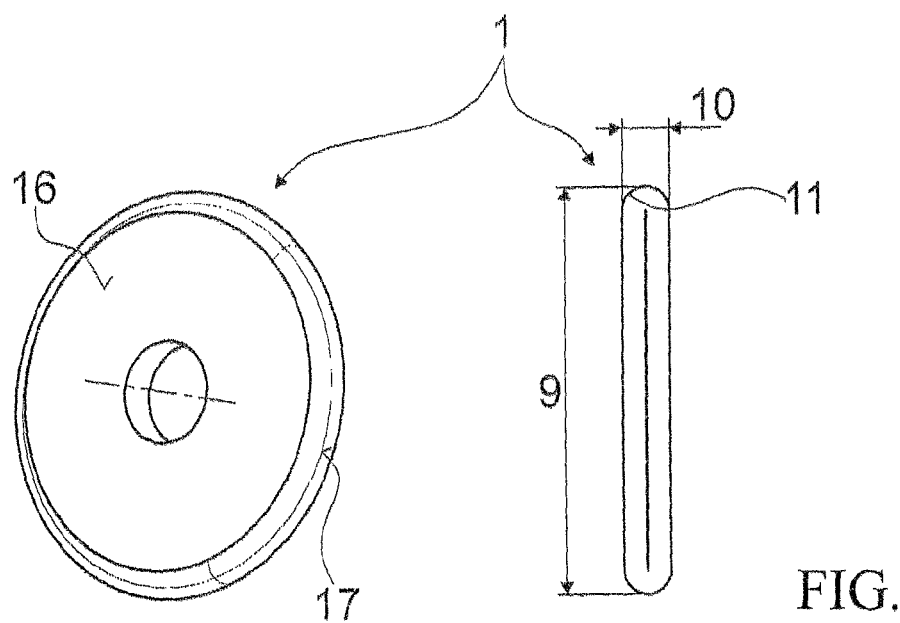

FIG. 1B shows an exemplary embodiment of the rotating disc 1 in a plan view and profile. The grinding disc or wheel 1 comprises two plane lateral surfaces 16 and an arched end face 17 connecting the lateral surfaces at the outer side. The material-removing effect of the rotating disc 1 is achieved by way of the two lateral surfaces 16 and the end face 17, which increases the machining speed in comparison to machining methods with a grinding pin. The profile of the rotating disc 1 shows the disc diameter 9, the disc width 10 and the radius of the arcuate end face 17. Sharp corners due to their notch effect increase the proneness of ceramic implants and ceramic attachment elements to breakage. The radius 11 is therefore advantageously selected in a large manner in relation to the disk width 10, for example with a ratio of the radius 11 to the disc width 10 of greater than 1 to 3 or in particular greater than 1 to 2. An exemplary embodiment of the grinding disc has a diameter 9 of 6.5 mm, a width 10 of 0.7 mm and a radius 11 of 0.35 mm. The arched or arcuate end face prevents the formation of sharp edges or corners in the inner structure and their notch effect. Ceramic implants and ceramic attachment elements with an inner structure manufactured with a grinding disc dimensioned in such a manner are therefore characterised by a particularly low proneness to breakage.

A further advantage of the method is that the rounding 18 at the face side of the slot 15 can be arranged very closely to the lateral surface 19 of the ceramic implant 5 or of the ceramic attachment element 6 without damaging the lateral surface. The slot depth in the region close to the rounding is very small due to the circular-arc-shaped recess of the slot and increases in the direction of the slot centre 14.

The rotational speed of the disc is selected in a region of 5,000 to 100,000 revolutions per minute, in particular from 10,000 to 60,000 revolutions per minute or from 20,000 to 40,000 revolutions per minute. Usually, the smaller the lateral surface of the grinding tool, the greater does the man skilled in the art select the rotational speed. Thus, he can optimise the material removal and achieve an optimal cutting speed in the region of 10 to 100 mm per minute for example. An inner structure arises by way of the advance of the rotating disc into the proximally accessible surface 7 of the implant 5 or into the end surface 8 of the attachment element 6. If the proximally accessible surface 7 or the end surface 8 is a closed surface, then by way of the advance, a slot 15 arises with a slot width 13 which corresponds to the disc width 10, and a rounding 18 at the face side of the slot, said rounding corresponding to the radius 11. The slot length 12 at the most is somewhat smaller than the disc diameter 9 if the rotation axis of the rotating disc runs centrically through the disc middle point or centre 3. A middle 14 of the slot opening is defined at half the length and half the width of the slot.

Figure 2A:
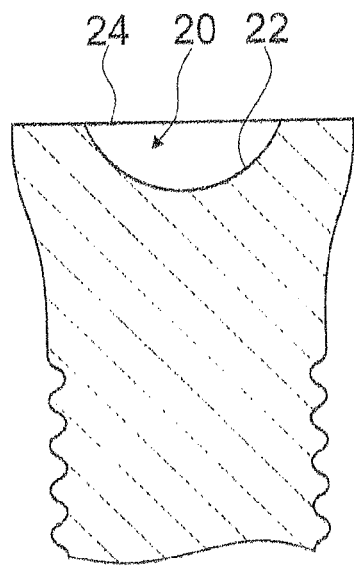
FIGS. 2A-2C illustrate method variants with different advance depth of the disc for an inner structure.
Figure 2B:
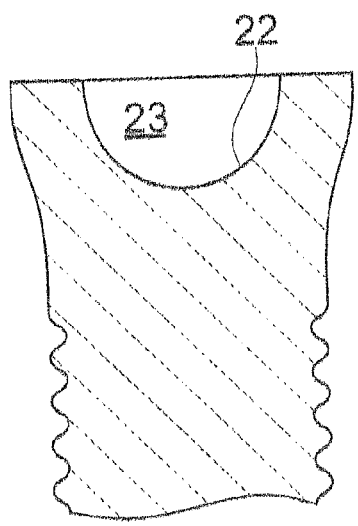
Figure 2C:
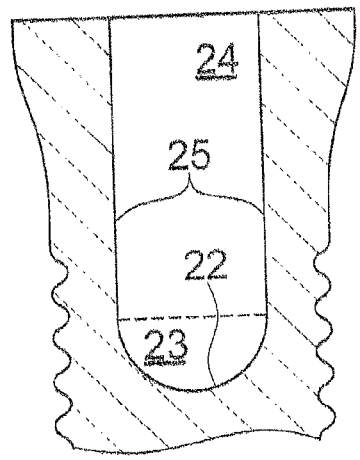

FIGS. 2A-2C show exemplary embodiments with a different advance depth of the disc 1. In some other embodiments of the method, as shown in FIG. 2A, the rotating disc 1 is driven for example via a centric rotation axis 2 and is advanced into the proximally accessible surface 7 of the ceramic implant 5 or into the end surface 8 of the ceramic attachment element 6 to a lesser extent than up to the disc middle point. In such embodiments of the method, a slot 15 arises, whose longitudinal section parallel to the advance direction 4 of the rotating disc 1 is a circle segment 20, which is delimited at the distal end by a circular arc 22 and in the proximally accessible surface by a chord 24.

In other embodiments, the disc 1 is advanced into the implant or the attachment element up to its middle point or deeper than up to its middle point. The disc 1 for example is driven via an eccentric rotation axis. In some embodiments, a central cavity exists (see also FIGS. 4A-5B) which provides space for a deflection gear.

In exemplary embodiments of the method, in which the rotating disc 1 is advanced into the proximally accessible surface 7 of the ceramic implant or into the end surface 8 of the ceramic attachment element, up to its middle point 3, a slot 15 arises, whose longitudinal section parallel to the advance direction 4 of the rotating disc 1 at the distal end has a circular arc 22 of a semicircle 23. In embodiments of the method, in which the rotating disc 1 is advanced into the proximally accessible surface deeper than up to its middle point, a longitudinal section arises, which at the distal end has the circular arc 22 of the semicircle 23 and which is delimited laterally in each case by a tangent to the semicircle parallel to the advance direction of the disc.

Figure 3A:
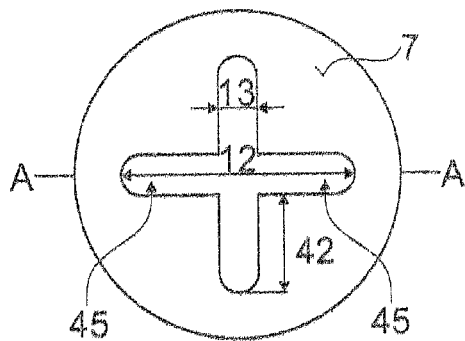
FIGS. 3A-3B illustrate an inner structure with 2 part-slots.
Figure 3B:
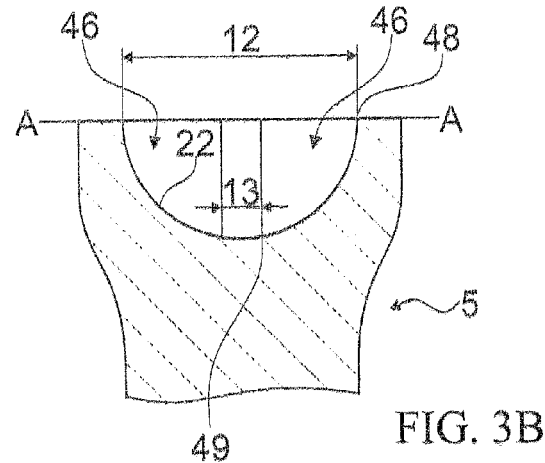
Figure 4A:
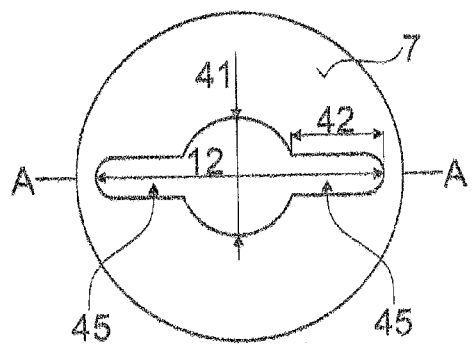
FIGS. 4A-4B illustrate an inner structure with cavity and two part-slots.
Figure 4B:
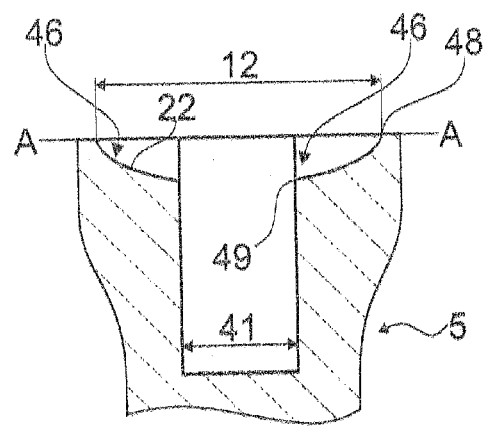
Figure 5A:
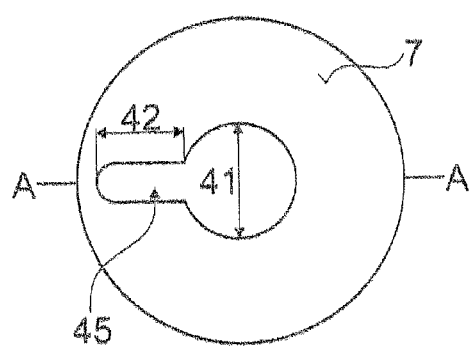
FIGS. 5A-5B illustrate an inner structure with cavity and one part-slot.
Figure 5B:
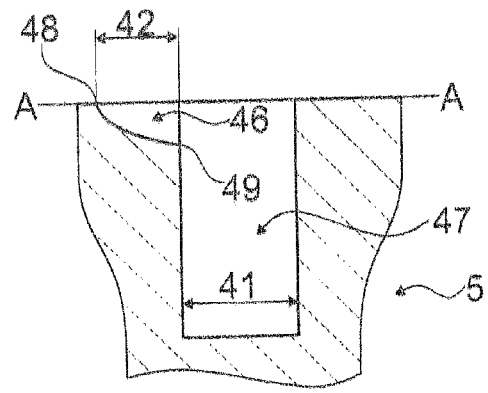

FIGS. 3A-5B show schematic representations of exemplary embodiments of inner structures with at least one part-slot 45. FIGS. 3A, 4A, and 5A show a view onto the proximally accessible surface of the implant 7, and FIGS. 3B, 4B, and 5B show a section through the ceramic implant 5, wherein the sections only show a proximal region of a two-part ceramic implant. The distal regions of the ceramic implant comprising for example a thread or cutting edges, in order to insert the ceramic implant into the bone, are not drawn. On account of its manufacture with a rotating disc 1, the part-slot 45 has the rounding 18 on a face side of the slot which faces the lateral surface of the implant or of the attachment element.

Of course, embodiments comprising part-slots 45 with sections of the circular arc 22 also in the end surfaces of ceramic attachment elements can also be manufactured.

FIGS. 3A-3B show an exemplary embodiment of an inner structure with two crossing slots, by which means four part-slots 45 are formed. The part-slots have a slot width 13. The initial slot length 12 is divided into two part-slot lengths 42 which, on account of the overlapping of the slots, is shorter than half the slot length 12. A longitudinal section through two part-slots that arose from a slot which was interrupted by a crossing with a second slot, parallel to the advance direction of the rotating disc, is then no longer a complete circle segment but two parts 46 of a circle segment which was interrupted by the width 13 of the crossing slot. Both parts 46 of the circle segment each have a section of a circular arc 22. An end point 48 of the section of the circular arc 22 lies in the proximally accessible surface. In similar embodiments of the ceramic attachment element 6 with a part-slot 45, the end point 48 of the section of the circular arc 22 analogously lies in the end surface 8 of the attachment element 6.

FIGS. 4A-4B show an exemplary embodiment of an inner structure with a cavity 47 and two part-slots 45. Such an inner structure is manufacturable in a proximally accessible surface 7 of a ceramic implant or of course also in an end surface 8 of an attachment element 6 which is not closed but is broken through by a cavity, in particular by a central cavity 47 of the implant or of the attachment element. In some embodiments which are not shown, the cavity not only opens into the proximally accessible surface, but also into a lateral surface of the ceramic implant.

In the shown embodiment in FIGS. 4A-4B, two part-slots 45 are shown, which for example were manufactured in a grinding step with a disc 1, wherein the disc 1 was advanced into the proximally accessible surface 7 interrupted by a cavity 47. The disc diameter 9 is greater than the diameter 41 of the cavity 47 at least by the part-slot length 42. Thus, right at the beginning, two part-slots 45 arise, which each have a section of the circular arc 22. Further pairs of parts-slots 45 can be created by way of further grinding steps with the disc 1. Of course, one could also firstly manufacture a slot or several slots with a grinding disc 1 and thereafter a cavity 47 which divides the slots in each case into 2 pairs of part-slots.

A longitudinal section through these two parts slots 45 parallel to the advance direction of the rotating disc is not a complete circle segment, which is to say segment of a circle, but it is two parts 46 of a circle segment which was interrupted by the diameter 41 of the cavity 47. Both parts 46 of the circle segment each have a section of the circular arc 22. An end point 48 of the section of the circular arc 22 lies in the proximally accessible surface 7, whereas the other end point 49 of the circular arc lies in the inside of the ceramic implant 5, or in analogous embodiments, in the inside of the ceramic attachment element 6, in particular on an inner wall of a cavity 47 of the ceramic implant or of a cavity 50 of the ceramic attachment element 6.

FIGS. 5A-5B show an exemplary embodiment an inner structure with a cavity 47 and with a part-slot 45. The length 42 of the part-slot 45 is selected such that it is smaller than half the diameter 41 of the cavity 47, so that the grinding disc 1 is advanced into the proximally accessible surface 7 of the implant 5 or into the end surface 8 of the attachment element 6 such that it contacts the border, which is to say edging of the cavity at the surface 7 or 8 at only one location and is advanced into the surface 7 or 8 at only one location, in order to manufacture embodiments of the ceramic implant 5 or of the ceramic attachment element 6 with an inner structure which only has one part-slot 45 or an odd number of part-slots 45. In this manner, only one part-slot 45 is created in a grinding step, wherein a longitudinal section through this part-slot 45 parallel to the advance direction of the rotating disc 1 does not represent a complete segment of a circle, but only a part 46 of a segment of a circle which is adjacent the cavity 47. The part 46 of the segment of a circle has a section of the circular arc 22. An end point 48 of the section of the circular arc 22 lies in the surface 7 or 8, while the other end point 49 of the circular arc lies in the inside of the ceramic implant or of the ceramic attachment element, in particular on an inner wall of a cavity 47 of the ceramic implant or of the ceramic attachment element.

Figure 6A:
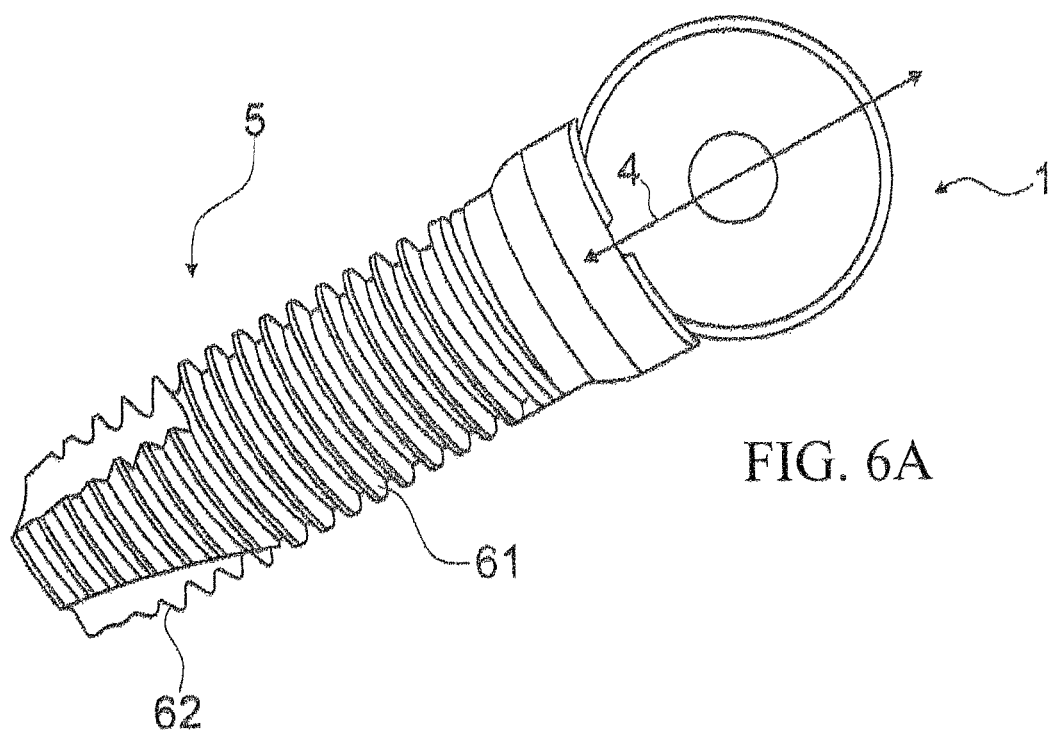
FIGS. 6A-6B are 3D representations for the manufacture of an inner structure in a proximal end surface of the ceramic implant, with a grinding disc.
Figure 6B:
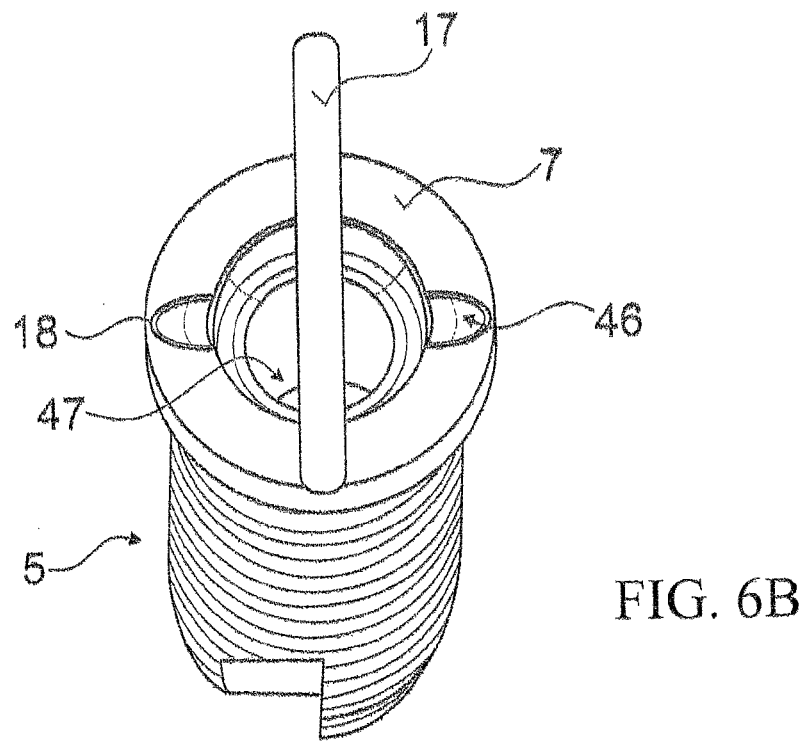

FIGS. 6A and 6B are 3D representations with regard to one embodiment of the manufacturing method of an inner structure in the proximally accessible end surface 7 of an exemplary two-part ceramic implant 5 that borders around a cavity 47. Two part-slots 45 arise by way of a first advance of the rotating disc 1 in an advance direction 4 perpendicularly to its rotation axis. The equally dimensioned disc 1 is advanced a second time into the proximally accessible surface, wherein the disc is rotated by 90° between the first and the second step. Thus for example, as illustrated, two parts of part-slots 45 arranged perpendicular to one another can be manufactured. Of course, further inner structures with an even number of part-slots can be manufactured by way of a similar method with further grinding steps, for example an inner structure with 8 parts-slots 45 with 4 grinding steps etc. The end face 17 of the grinding disc 1 shapes the rounding 18 of the face side of the part-slots 45 which faces the lateral surface.

A great advantage of the invention is the fact that such inner structures can be created with a grinding disc (grinding wheel), in particular with a shaped grinding disc, within a very short time. The machining time, for example, for the manufacture of an inner structure as an insertion geometry, rotation lock and/or positioning structure with one slot or two part-slots is typically less than three minutes, in particular less than one minute. Inner structures such as the inner structure with two slots or four parts slots and which is represented in FIGS. 6A-6B are manufacturable, for example, in one to three minutes.

The inner structure of the ceramic implant of a two-part or multi-part implants system and which is represented by way of example in FIGS. 6A-6B serves as an insertion geometry which cooperates with an insertion tool. The exemplary ceramic implant 5 comprises a thread 61 and cutting edges 62. In some embodiments, the inner structure also serves as a positioning structure in cooperation or interaction with an attachment element.

The ceramic implant represented by way of example in FIGS. 6A-6B, in the proximal region comprises the inner structure with the four part-slots 45, and a cavity 47 with an inner wall having annular recesses. Such annular recesses are advantageous for bonded, two-part implants since the bonding agent has space in these recesses.

FIGS. 7A-8B are sectioned drawings of exemplary embodiments of an implant system. FIG. 7A represents an exemplary ceramic implant with an inner structure and FIG. 7B an exemplary attachment element with an outer structure, wherein the attachment element with the outer structure can, but not necessarily be of ceramic. FIG. 8A shows an implant with an exemplary outer structure, wherein the implant can, but not necessarily be of ceramic. FIG. 8B shows an exemplary ceramic attachment element with an inner structure.

The attachment element 6 represented in FIGS. 7A-7B comprises an inner cone 72 which is inserted into the implant 7. The attachment element 6 represented in FIGS. 8A-8B comprises an outer cone 73 which is placed onto the implant. In the shown embodiment, the connection between the implant 5 and the attachment element 6 is a bonded connection, thus it is an at least two-part, bonded implant system. Of course attachment elements 6 as an inner and outer cone 73 for implants 5 with a screw connection are also the subject matter of this invention, and the cavities 47 and 50 do not have to be an inner cone 72 but can also be an inner cylinder or a differently shaped inner cavity. In the case of a screwed connection between the attachment element and the implant, common threaded bores and screws as known in the state of the art can be used (see also FIG. 10).

The inner structures represented in FIGS. 7A-8B are manufacturable in one grinding step with the represented grinding disc 1 and after removal of the disc comprise two part-slots 45, with a circular arc section 22. The part-slots 45 run out into a conical cavity 47 of the ceramic implant 5 or into an inner cavity 50 of the ceramic attachment element 6 which is open for example at two sides in the represented embodiment in FIG. 8b.

Corresponding to the inner structures, the represented outer structures comprise two wings 71 which can be actively connected to the part-slots 45. The wings 71 of the represented attachment element of a bonded implant system serve as a positioning structure for the connection of the attachment element 6 to the implant 5. Of course, inner structures with other radii of the grinding disc or a different advance depth of the disc can be manufactured with this method. Of course, inner structures without a cavity 47, with one slot 15 with a part-slot or with more than two part-slots and described in the above figures can also be manufactured.

FIGS. 9A-10D show an exemplary embodiment for a bonded and a screwed connection between an implant and an attachment element comprising an inner cone 72 which is inserted into the implant.

FIGS. 9A-9F: An embodiment example of a bonded, at least two-part implant system:

FIG. 9A shows a view of an exemplary pin-like ceramic implant 5, FIG. 9B shows a section through the implant 5 and FIG. 9C shows a view onto the face side at the proximal end 91 of the ceramic implant 5. The face side 91 comprises the proximally accessible surface 7 which annularly borders around a central cavity 47. The inner structure comprises four part-slots 45. This inner structure is the insertion geometry, in order to rotate the ceramic implant into a bone tissue. The exemplary ceramic implant 5 in a distal region 92 with a thread 94 comprises cutting edges 95 which lead to the distal end 93. The lateral surface 99 of this embodiment of the ceramic implant 5 of an at least two-part implant system, except for the proximally accessible surface 7 is essentially surrounded by bone tissue after the implantation.

Figure 9F:
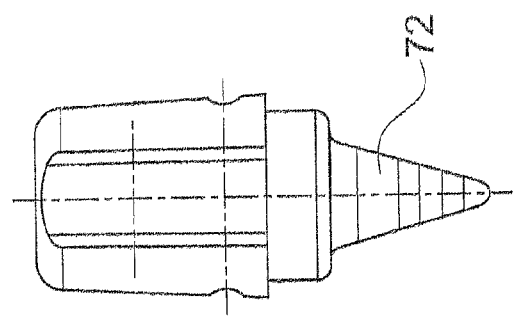
FIG. 9F is a view onto the attachment element.
Figure 9E:
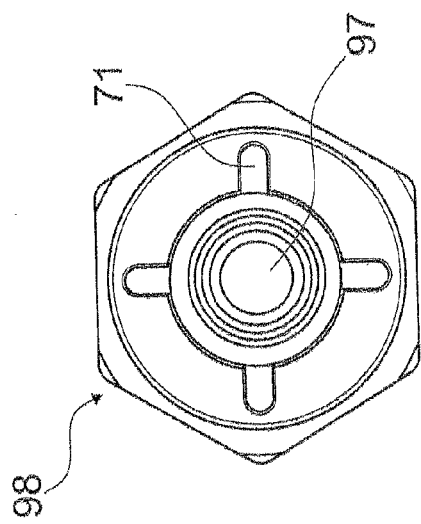
FIG. 9E is a view of the insertion tool of FIG. 9D from a distal direction.
Figure 9D:
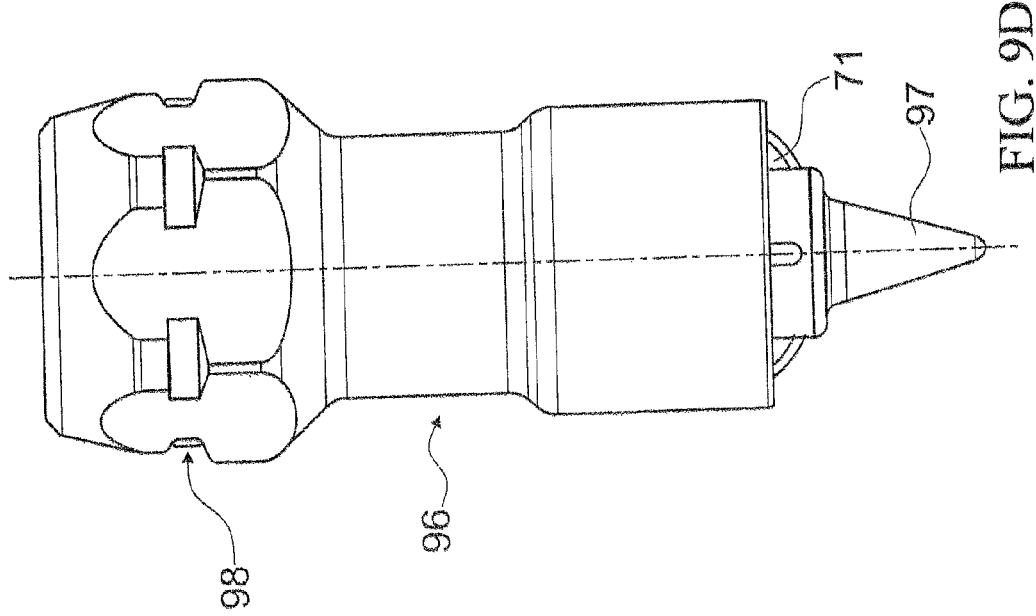
FIG. 9D is a lateral view of an insertion tool.

FIG. 9D shows an exemplary insertion tool 96 with an inner cone 97 and an outer structure with four wings 71 which engage into the implant. The inner cone can be introduced into the cavity 47 of the ceramic implant 5. Thereby, the four wings 71 of the outer structure of the insertion tool 96 engage into the four part-slots 45 of the ceramic implant and transmit a rotation force exerted onto the tool 96, onto the ceramic implant 5. The rotation force is exerted onto the tool for example by way of an electric or mechanical toothed ratchet, wherein the toothed ratchet has an inner structure that engages on the outer structure 98 in the proximal region of the tool 96. FIG. 9E shows a plan view of the tool seen from the distal side. FIG. 9F shows a view onto an exemplary ceramic attachment element 6 for the ceramic implant 5, with an inner cone which engages into the cavity 47 of the ceramic implant and is fastened on the implant with a bonding connection.

FIGS. 10A-10D show an example for a screwed, at least two-part implant system.

Figures 10A, 10B, 10C, 10D:
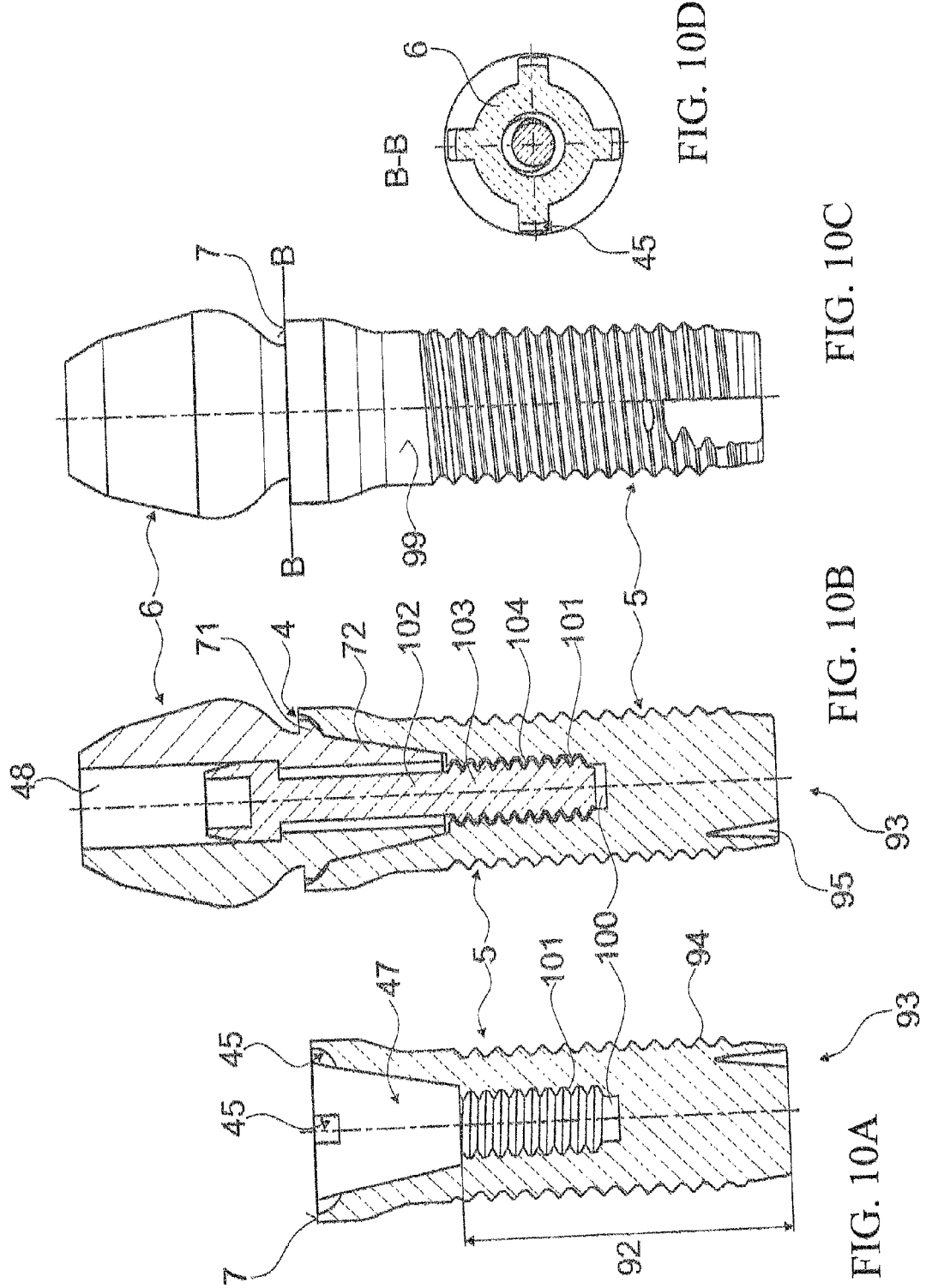
FIG. 10A is a section through a screwed, two-part implant system.
FIG. 10B is a section through the implant and attachment element.
FIG. 10C is a view of the implant and attachment element.
FIG. 10D is a view/section: B-B of FIG. 10C.

FIG. 10A shows a section through an exemplary pin-like ceramic implant 5, FIG. 10B shows a section through a exemplary, screwed, at least two-part implant system with the implant 5 and the attachment element 6 and FIG. 10C shows a view of the exemplary ceramic implant system and FIG. 10D shows a view onto the section plane B-B of FIG. 10C, which means to say onto the proximal end surface 7 of the ceramic implant and onto a section plane through the screwed-in attachment element 6.

The proximally accessible surface 7 of the pin-like ceramic implant borders around or surrounds a central, conical cavity 47 which at its distal end goes into a further central cavity which is cylindrical. The ceramic implant has an inner structure with four part-slots 45 that serve as an insertion geometry in order to rotate the ceramic implant 5 into a bone tissue. The exemplary ceramic implant 5 in a distal region 92 comprises an outer thread 94 and cutting edges 95 leading towards the distal end 93.

FIG. 10B by way of example shows how a screw 103 for the connection of the attachment element 6 to the implant 5 can be led through the conical cavity 47 of this implant, into the cylindrical cavity 100, said conical cavity 47 being provided for the inner cone 72 of the attachment element 6. The cylindrical cavity 100 comprises an inner thread 101 and the screw 103 comprises an outer thread 104. FIG. 10C shows a view onto the exemplary two-part implant system of the lateral surface 99 and of the proximally accessible surface 7 of the ceramic implant 5. The lateral surface 99 of this embodiment of the ceramic implant 5 apart from the proximally accessible surface 7 is essentially surrounded by bone tissue after the implantation. FIG. 10D shows a view onto the section plane B-B of FIG. 10C, which is to say onto the proximal end surface 7 of the ceramic implant and onto a section plane through the screwed-in attachment element 6 and with the part-slots 45 of the inner structure that serves as an insertion geometry and as a rotation lock.

The invention claimed is:

1. A method for manufacturing an inner structure of a ceramic implant, the inner structure comprising a slot, the method comprising the steps of:
    providing an implant, the implant being a ceramic dental implant, the implant having an apical region equipped to be implanted in bone tissue of a jawbone, wherein the apical region ends in an apical end, the implant extending along a proximodistal axis between the apical end and a coronal end face, wherein a periphery of the coronal end face is limited by an end face edge;
    providing a rotating disc;
    orienting a rotation axis of the rotating disc at an angle to the proximodistal axis; and,
    advancing the rotating disc in a direction perpendicular to the rotation axis into the implant through the coronal end face and thereby removing ceramic material of the implant until the implant comprises the slot in the coronal end face and extending from the coronal end face towards the apical end, the slot being formed in the coronal end face at a location spaced inwardly from the periphery thereof so as to not reach to the end face edge, and a bottom of the slot being delimited apically by a concave surface that is rounded in two dimensions.

2. The method according to claim 1, wherein the rotating disc is advanced less deeply than up to a middle point of the rotating disc.

3. The method according to claim 1, wherein the ceramic implant is sintered before the manufacture of the at least one inner structure.

4. The method according to claim 1, wherein the ceramic implant is sintered after the manufacture of the at least one inner structure.

5. The method according to claim 1, wherein the ceramic implant defines a cavity that opens in the proximally accessible surface of the ceramic implant and wherein the proximally accessible surface borders around the opening of the cavity.

6. The method according to claim 1, wherein the ceramic implant is a pin-like ceramic implant.

7. The method according to claim 1, wherein an outer cutting circumference of the rotating disk is arched.

8. The method according to claim 1, wherein the coronal end face is perpendicular to the proximodistal axis.

* * * * *

UNITED STATES PATENT AND TRADEMARK OFFICE
CERTIFICATE OF CORRECTION

PATENT NO. : 9,943,385 B2
APPLICATION NO. : 14/035330
DATED : April 17, 2018
INVENTOR(S) : Ernst Thomke et al.

It is certified that error appears in the above-identified patent and that said Letters Patent is hereby corrected as shown below:

On the Title Page

Item (73) Assignee:
Change "Z-SYSTEMS SCHWEIK AG" to --Z-SYSTEMS SCHWEIZ AG--.

Signed and Sealed this
Twenty-second Day of May, 2018

Andrei Iancu
*Director of the United States Patent and Trademark Office*